United States Patent [19]

Wiley

[11] Patent Number: 4,520,191

[45] Date of Patent: May 28, 1985

[54] PAULOMYCIN DERIVATIVES

[75] Inventor: Paul F. Wiley, Portage, Mich.

[73] Assignee: The Upjohn Company, Kalamazoo, Mich.

[21] Appl. No.: 549,939

[22] Filed: Nov. 8, 1983

[51] Int. Cl.³ .............................................. C07H 15/22
[52] U.S. Cl. .................................... 536/17.9; 536/4.1; 536/16.8; 536/17.2; 536/17.5; 536/18.1; 536/18.7; 536/53
[58] Field of Search ................... 536/16.8, 17.9, 18.1, 536/18.7, 4.1, 53

[56] References Cited

U.S. PATENT DOCUMENTS 4,335,108  6/1982  Argoudelis et al. ................ 424/117

*Primary Examiner*—Johnnie R. Brown
*Assistant Examiner*—Elli Peselev
*Attorney, Agent, or Firm*—Lawrence T. Welch; Roman Saliwanchik

[57] ABSTRACT

Novel and useful compounds are obtained by the degradation of antibiotics paulomycin A and paulomycin B. These novel compounds are useful as ultraviolet light filters in plastics, cloth, and the like.

4 Claims, No Drawings

PAULOMYCIN DERIVATIVES

BACKGROUND OF THE INVENTION

Paulomycin A and B are well-known antibiotics producible by fermentation means as disclosed in U.S. Pat. No. 4,335,108. Example 1 of the patent discloses the fermentation process and recovery of paulomycins A and B. Examples 2 and 3 disclose the isolation processes for preparing the essentially pure crystalline preparations of paulomycin A and paulomycin B, respectively. The antibiotics are characterized by physical and chemical parameters.

BRIEF SUMMARY OF THE INVENTION

The structural formulas for paulomycin A and B have been determined as shown in Chart 1. Upon subjecting these antibiotics to various degradative conditions, there are obtained novel useful compounds. The novel compounds are named paulomycinone A and B; methoxypaulomycinone A and B; paulomenol A and B; and paulinone. This lastnamed compound can be obtained when either paulomycin A or B are the starting materials in the degradative process.

DETAILED DESCRIPTION OF THE INVENTION

The obtention of the novel compounds of the subject invention is schematically shown in Chart 2. Specific reaction conditions wherein paulomycin A is used as the starting material are given in the examples following. The same reaction conditions can be used to obtain the novel degradative products of paulomycin B when paulomycin B is used as the starting material.

The novel compounds of the subject invention are useful as UV absorbents in technical and industrial areas, as follows:

(a) textile materials, for example, wool, silk, cotton, hemp, flax, linen, and the like; and (b) natural or synthetic resins.

Depending on the nature of the material to be treated, the requirements with regard to the degree of activity and durability, and other factors, the proportion of the light screening agent to be incorporated into the material may vary within fairly wide limits, for example, from about 0.01% to about 10%, and, advantageously, 0.1% to 2% of the weight of the material which is to be directly protected against the action of UV rays.

Hereinafter are described non-limiting examples of the process and products of the subject invention. All percentages are by weight, and all solvent mixture proportions are by volume unless otherwise noted.

EXAMPLE 1

Paulomycinone A

A solution of 2.0 g of paulomycin A in 200 ml of $CH_3OH$ was allowed to stand at room temperature for 5 days. The solution was evaporated to dryness in vacuo, and the residue was chromatographed on 200 g of silica gel eluting with $CHCl_3$-$CH_3OH$ (94:6). A total of 99 five-ml fractions were collected. On the basis of tlc in $CHCl_3$-$CH_3OH$ (92:8) fractions 24–29 were combined as paulomycinone A, $R_f$ 0.67. The combined fractions were evaporated in vacuo to give 663 mg. This material was combined with 407 mg of similarly prepared material and chromatographed as above. Fractions 48–57 were combined on the basis of tlc and evaporated in vacuo, yield 1.00 g; mp 57°–73°; $[\alpha]_D$ 2° (c 0.694, $CH_3OH$); UV ($CH_3OH$) 232 nm ($\epsilon$ 15,250), 264 nm ($\epsilon$ 18,400), 440 nm ($\epsilon$ 2100); IR (Nujol) 3488, 3363, 3235, 3249, 2037, 1735, 1695, 1637, 1618, 1569, 1461, 1378, 1367, 1341, 1264, 1240, 1187, 1154, 1115, 1096, 1056, 1023, 998, 989, 890, 870, 751, 722 cm$^{-1}$; $^1$H NMR ($CD_3COCD_3$) δ 0.91 (3 H, t, J=6.4 Hz, H-5'''), 1.15 (3 H, d, J=8.4 Hz, H-4'''), 1.31 (3 H, d, J=6.4 Hz, H-6'), 1.35 (3 H, d, J=7.2 Hz, H-8'), 1.50, 1.73 (2 H, 2 m, H-3'''), 1.97 (3 H, d, J=8.0 Hz, H-4''), 2.04 (3 H, s, H-2''''), 1.90, 2.43 (2 H, 2 m, H-2'), 2.42 (1 H, m, H-2'''), 2.93 (1 H, s, exch.), 3.39 (3 H, s, $CH_3O$), 3.50 (1 H, m, H-9), 3.70 (2 H, m, H-13), 4.27, 4.46, 4.62 (5 H, 3 m, H-10, H-12, exch.), 5.06, 5.12 (3 H, m, H-8, H-1', exch.), 5.41 (1 H, m, H-11), 6.42 (1 H, q, J=8.0 Hz, H-3''), 6.47 (1 H, s, H-5), 8.66, 10.00 (2 H, 2 broad s, $NH_2$), 13.09 (1 H, s, enolic); $^{13}$C NMR ($CDCl_3$) δ 185.12 (C-4), 180.51 (C-7), 175.79 (C-1'''), 170.60 (C-1''''), 168.62 (C-1), 160.5 (C-1''), 152.9 (C-3), 151.96 (C-6), 136.06 (C-3''), 129.59 (C-5), 123.44 (C-2''), 100.30 (C-1'), 97.25 (C-2), 80.03 (C-8), 79.64 (C-4'), 74.06 (C-10), 73.59 (C-3'), 72.47 (C-12), 70.82 (C-11), 70.58 (C-7'), 70.25 (C-9), 69.08 (C-5'), 62.64 (C-13), 57.6 ($CH_3O$), 41.56 (C-2'''), 30.85 (C-2'), 26.77 (C-3'''), 20.76 (C-2''''), 16.65 (C-4''), 15.73 (C-6', 6-8'), 14.68 (C-4''), 11.75 (C-5'''); mass spectrum m/z 768 (M$^+$).

Anal. Calcd. for $C_{34}H_{44}N_2O_{16}S$: C, 53.12; H, 5.77; N, 3.60; S, 4.17. Found: C, 52.43; H, 5.99; N, 3.58; S, 4.17.

EXAMPLE 2

Methoxypaulomycinone A

A solution of 500 mg of paulomycin A in 50 ml of $CH_3OH$ was refluxed for 22 hours. It was then evaporated to dryness in vacuo. The residue was chromatographed on 50 g of silica gel eluting with $CHCl_3$-$CH_3OH$ (94:6) and collecting 36 five-ml fractions. On the basis of tlc in $CHCl_3$-$CH_3OH$ (92:8), fractions 25–34 were combined as methoxypaulomycinone, A, $R_f$ 0.55. Evaporation in vacuo gave 276 mg; mp 93°–101°; $[\alpha]_D$ 29° (c 0.8385, $CH_3OH$); UV ($CH_3OH$) 244 sh nm ($\epsilon$ 17,410), 257 nm ($\epsilon$ 17,450), 441 nm ($\epsilon$ 2240); IR (Nujol) 3551, 3253, 3217, 1731, 1698, 1656, 1618, 1570, 1504, 1265, 1240, 1215, 1191, 1151, 1116, 1097, 1057, 1025, 993, 956, 916, 890, 868, 824, 783, 753, 721, 690, 673, 635 cm$^{-1}$; $^1$H NMR ($CDCl_3$) δ 0.90 (3 H, t, J=8.1 Hz, H-5'''), 1.17 (3 H, d, J=7.2 Hz, H-4'''), 1.36 (6 H, d, J=6.6 Hz, H-6', H-8), 1.60 (2 H, m, H-3'''), 1.83 (3 H, d, J=6.9 Hz, H-4''), 2.06 (3 H, s, H-2''''), 2.38 (1 H, m, H-2'), 3.44 (3 H, s, $CH_3O$ at C-3'), 3.56 (1 H, m, CHO), 4.03 (3 H, s,

$$CH_3O\overset{\overset{S}{\|}}{C}),$$

4.22 (4 H, m, CHO), 4.83 (3 H, m, CHO), 5.35 (1 H, q, J=6.6 Hz, H-7'), 6.88 (1 H, q, J=6.9, H-3''), 6.94 (1 H, s, H-5), 7.55, 9.92 (2 H, 2 broad s, $NH_2$), 13.20 (1 H, s, enolic); $^{13}$C NMR ($CDCl_3$) 185.2 (C-4), 180.6 (C-7), 176.01 (C-1'''), 170.82 (C-1''''), 168.81 (C-1), 162.54 (C-1''), 152.23 (C-3, C-6), 137.94 (C-3''), 129.70 (C-5), 128.2 (C-2''), 100.40 (C-1'), 97.20 (C-2), 80.3 (C-8), 74.20 (C-3', C-10), 73.70 (C-4), 72.77 (C-12), 70.66 (C-11, C-7'), 69.39 (C-9), 69.13 (C-5'), 63.05 (C-13), 58.27, 57.63 (2 $CH_3O$), 41.61 (C-2'''), 30.37 (C-2'), 26.78 (C-3'''), 20.84 (C-2''''), 16.68 (C-4''), 15.70 (C-6', C-8), 14.04 (C-4'''), 11.70 (C-5'''); mass spectrum m/z 800 (M$^+$).

Anal. Calcd for $C_{35}H_{48}N_2O_{17}S$: C, 52.49; H, 6.04; N, 3.50; S, 4.01. Found C, 51.22; H, 5.92; N, 3.36; S, 3.66.

This same compound was also obtained as the more polar fraction obtained in the chromatography of paulomycinone.

EXAMPLE 3

Paulomenol A

A solution of 786 mg (1 mmole) of paulomycin A in 500 ml of 0.01 $N(CH_3)_3N$ was prepared by stirring a mixture of the two. The solution was allowed to stand at room temperature for 2 days followed by filtration. The filtrate was extracted with four 250-ml portions of $CHCl_3$. The aqueous phase was adjusted to pH 3 with HCl, and the extraction was repeated. All of the extracts were combined and evaporated to dryness in vacuo, yield 449 mg. This was combined with 458 mg obtained in a similar run and chromatographed on 131 g of silica gel eluting with $CHCl_3$-$CH_3OH$ (85:15) collecting 146 four-ml fractions. The fractions (67–146) containing paulomenol A were determined by tlc using $CHCl_3$-$CH_3OH$-$H_2O$ (78:20:2, $R_f$ 0.31). These fractions were combined and evaporated in vacuo to give 521 mg. This was recrystallized from a mixture of $CHCl_3$ and Skellysolve B and finally from $CHCl_3$, yield 202 mg; mp 187°–191°; UV ($C_2H_5OH$) 241 nm ($\epsilon$ 8590), 318 nm ($\epsilon$ 8860); IR (Nujol) 3300, 3270, 1730, 1695, 1580, 1305, 1245, 1190, 1105, 1045, 995, 900, 760 cm$^{-1}$; $^1$H NMR ($CD_3COCD_3$) $\delta$ 0.98 (3 H, t, J=6.0 Hz, H-5'''); 1.21 (3 H, d, J=8.0 Hz, H-4'''), 1.29 (3 H, d, J=6.0 Hz, H-6'), 1.31 (3 H, d, J=6.3 Hz, H-8'), 1.64 (2 H, m, H-3'''), 1.92, 2.27 (2 H, 2 m, H-2'), 2.04 (3 H, s, H-2''''), 2.46 (1 H, m, H-2'''), 3.16 (2 H, dd, H-5), 3.34 (3 H, s, $CH_3O$), 3.41 (1 H, s, exch), 3.49 (2 H, m, H-9 and H-11), 3.65 (1 H, m, H-3'), 3.73 (2 H, m, H-13), 3.92 (1 H, d, J=8.0 Hz, H-8), 4.08 (1 H, m, H-12), 4.10 (1 H, m, H-10), 4.30 (1 H, d, exch.), 4.49 (1 H, q, J=6.0 Hz, H-5'), 5.06 (1 H, d, exch.), 5.17 (1 H, q, H-1'), 5.25 (1 H, s, exch.), 5.39 (1 H, q, J=6.3 Hz, H-7'), 8.37, 9.88 (2 H, 2 broad s, NH$_2$); $^{13}$C NMR ($CD_3COCD_3$) $\delta$ 198.61 (C-4), 188.02 (C-7), 175.06 (C-1'''), 170.48 (C-1''''), 169.40 (C-1), 159.46 (C-3), 99.90 (C-2), 99.66 (C-1'), 80.67 (C-10), 78.34 (C-4'), 78.25 (C-8), 75.04 (C-12), 74.34 (C-3'), 73.53 (C-6), 69.86 (C-7'), 69.72 (C-11), 67.90 (C-5'), 67.60 (C-9), 63.42 (C-13), 56.58 ($CH_3O$), 48.12 (C-5), 41.53 (C-2'''), 30.23 (C-2'), 26.71 (C-3'''), 20.08 (C-2''''), 16.68 (C-4'''), 15.35 (C-6' and C-8'), 11.36 (C-4'''); mass spectrum (TMS derivative) m/z 949.4221 (Calcd for $C_{41}H_{75}NO_{16}Si_4$, 949.41636).

Anal. Calcd for $C_{29}H_{43}NO_{16}$: C, 52.64; H, 6.55; N, 2.12. Found: C, 50.86; H, 6.49; N, 2.02.

EXAMPLE 4

Paulinone

One gram of a mixture of paulomycins A and B was dissolved in 125 ml of $CH_3OH$ 1N in HCl. After the solution had stood at room temperature for 3 hours, it was neutralized by slow addition of 34.4 g of $Ag_2CO_3$ with stirring. The mixture was filtered, and the insoluble material was washed thoroughly with $CH_3OH$. The filtrate was evaporated to dryness in vacuo, and the residue was mixed with 100 ml of 60% $CH_3OH$. The insoluble material was removed by filtration and the filtrate was extracted with four 50-ml portions of cyclohexane. The aqueous phase was concentrated in vacuo until the $CH_3OH$ was removed. The residue was filtered, and the filter cake was air dried giving 363 mg of an orange solid.

The crude product was chromatographed on 36 g of acid-washed silica gel eluting with $CHCl_3$-$CH_3OH$ (9:1) and collecting 24 five-ml fractions. On the basis of tlc in methyl ethyl ketone-acetone-water (70:20:11; $R_f$ 0.59), fractions 17–21 were combined and evaporated in vacuo, yield 200 mg. Recrystallization from $CH_3OH$ gave 100 mg; mp 157°–160°; $[\alpha]_D$ 108° (c 0.2835, $CH_3OH$); UV ($CH_3OH$) 231 nm ($\epsilon$ 15,400), 266 nm ($\epsilon$ 18,050), 438 nm ($\epsilon$ 1700); IR (Nujol) 3511, 3436, 3417, 3327, 2050, 1722, 1696, 1682, 1644, 1634, 1617, 1568, 1512, 1268, 1247, 1181, 1166, 1120, 1075, 1072, 1049, 1039, 909, 900, 827, 751, 747, 622 cm$^{-1}$; $^1$H NMR ($CD_3COCD_3$) $\delta$ 1.96 (3 H, d, J=7.2 Hz, H-4'), 3.61 (3 H, m, H-9, H-13), 4.05 (1 H, m, H-12), 4.45 (1 H, m, H-10), 4.97 (2 H, m, H-11, exch.), 5.06 (1 H, d, J=8.6 Hz, H-8), 6.85 (1 H, q, J=7.2 Hz, H-3'), 7.06 (1 H, s, H-5), 8.56 (1 H, s, NH), 9.93 (1 H, s, NH), 13.40 (1 H, s, enolic); $^{13}$C NMR ($CD_3OD$) $\delta$ 186.69 (C-4), 182.0 (C-7), 171.15 (C-1'), 162.12 (C-1), 154.79 (C-3), 153.03 (C-6), 144.1 (C-5'), 136.49 (C-3'), 131.83 (C-5), 125.10 (C-2'), 97.0 (C-2), 75.10 (C-8), 74.76 (C-10), 72.75 (C-12), 71.01 (C-11), 69.83 (C-9), 62.44 (C-13), 14.63 (C-4'); mass spectrum m/z 454 (M+). Anal. Calcd. for $C_{18}H_{18}N_2O_{10}S$: C, 47.58; H, 4.00; N, 6.12; S, 7.06. Found: C, 47.11; H, 4.11; N, 5.99; S, 6.95.

CHART 1

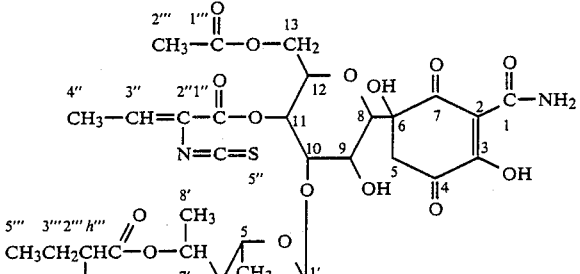

PAULOMYCIN A

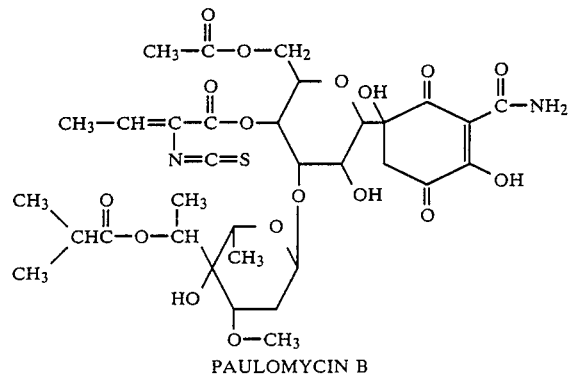

PAULOMYCIN B

CHART 2
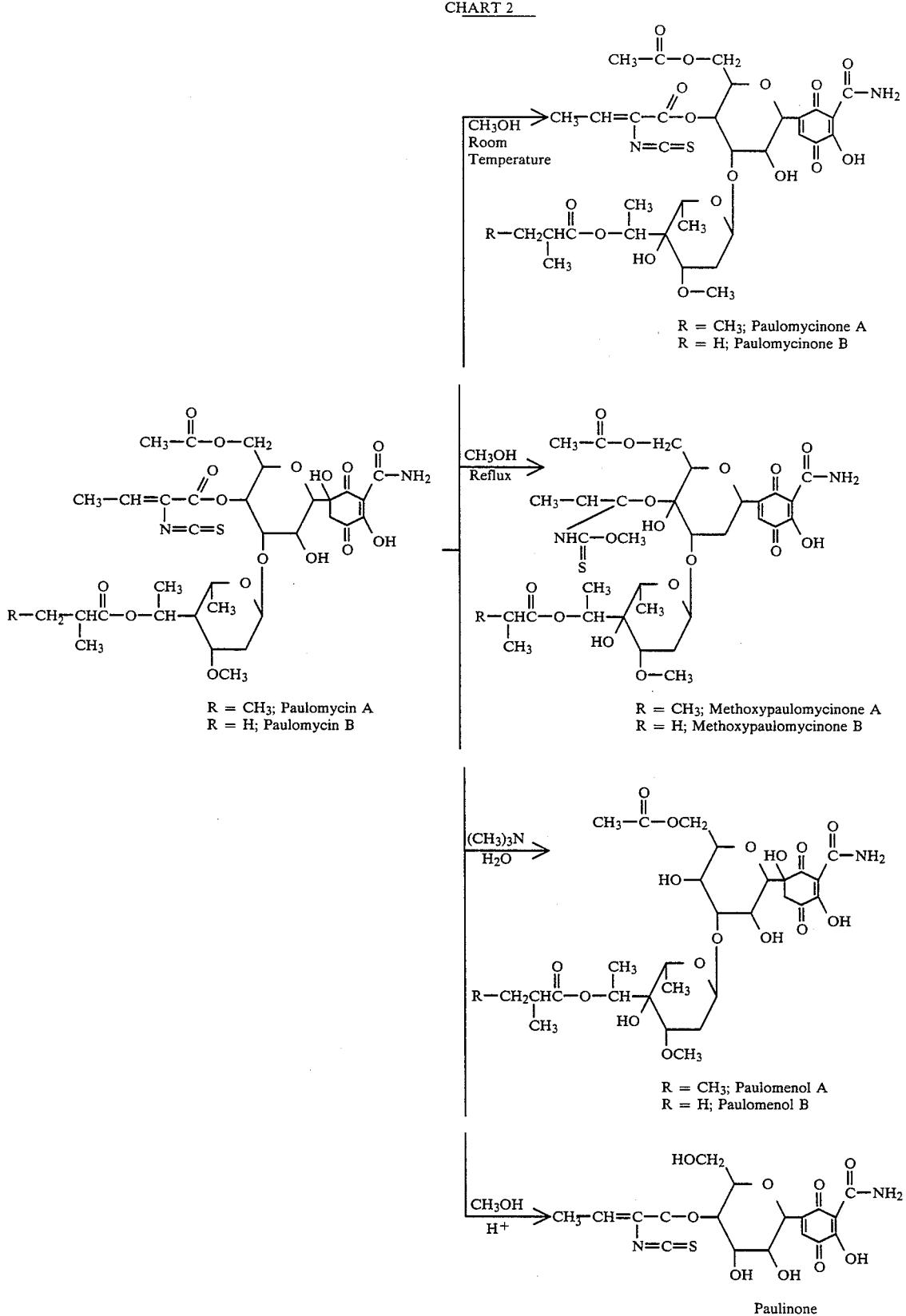
R = CH₃; Paulomycinone A
R = H; Paulomycinone B
R = CH₃; Paulomycin A
R = H; Paulomycin B
R = CH₃; Methoxypaulomycinone A
R = H; Methoxypaulomycinone B
R = CH₃; Paulomenol A
R = H; Paulomenol B
Paulinone
I claim:
1. A compound of the formula

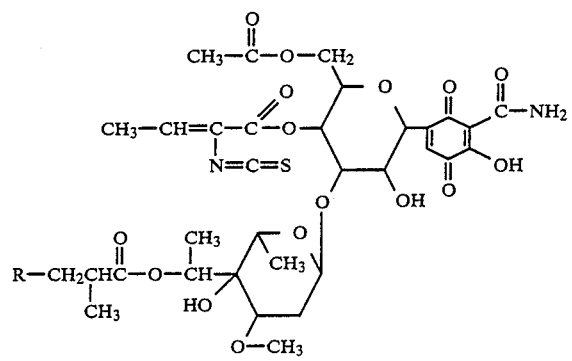
wherein R is H or CH₃.
2. A compound of the formula
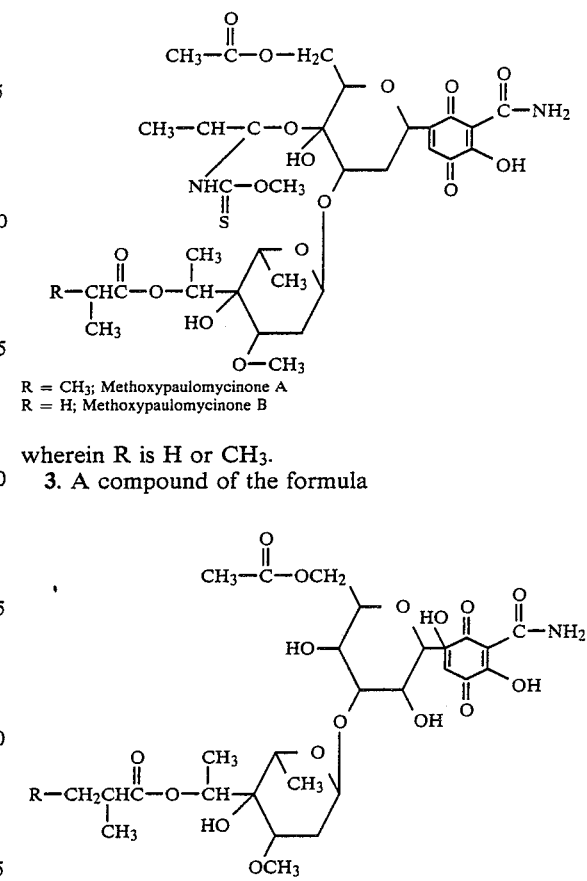
R = CH₃; Methoxypaulomycinone A
R = H; Methoxypaulomycinone B
wherein R is H or CH₃.
3. A compound of the formula
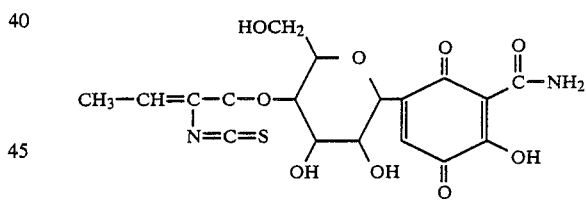
wherein R is H or CH₃.
4. A compound of the formula
Paulinone
* * * * *

UNITED STATES PATENT OFFICE
CERTIFICATE OF CORRECTION

Patent No. 4,520,191           Dated 28 May 1985

Inventor(s) Paul F. Wiley

It is certified that error appears in the above-identified patent and that said Letters Patent are hereby corrected as shown below:

Column 2, line 48, "H-8)," , should read -- H-8'), --.
Column 2, line 64, "(C-4)," should read -- (C-4'), --.
Column 3, line 51, "(C-4''');" should read -- (C-5'''); --.
Column 8, Claim 3, lines 26-28, that portion of the formula should
   read as follows:

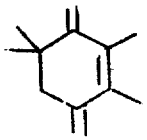

Signed and Sealed this

Twenty-ninth Day of July 1986

[SEAL]

Attest:

DONALD J. QUIGG

Attesting Officer      Commissioner of Patents and Trademarks